(12) United States Patent
Madsen

(10) Patent No.: US 9,138,510 B2
(45) Date of Patent: *Sep. 22, 2015

(54) STERILIZED READY-TO-USE CATHETER

(71) Applicant: Coloplast A/S, Humlebaek (DK)

(72) Inventor: Niels Joergen Madsen, Alleroed (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,910

(22) Filed: May 13, 2014

(65) Prior Publication Data

US 2014/0249489 A1  Sep. 4, 2014

Related U.S. Application Data

(60) Continuation of application No. 11/134,304, filed on May 23, 2005, now abandoned, which is a division of application No. 09/862,030, filed on May 18, 2001, now Pat. No. 6,986,868, which is a continuation-in-part of application No. PCT/DK99/00641, filed on Nov. 19, 1999, which is a continuation-in-part of application No. 09/218,305, filed on Dec. 22, 1998, now abandoned.

(30) Foreign Application Priority Data

Nov. 20, 1998 (DK) .................. 1998 01534

(51) Int. Cl.
| | |
|---|---|
| *B65D 81/24* | (2006.01) |
| *B32B 1/02* | (2006.01) |
| *A61L 29/14* | (2006.01) |
| *A61L 2/08* | (2006.01) |
| *A61L 2/10* | (2006.01) |
| *A61L 29/08* | (2006.01) |
| *A61M 25/00* | (2006.01) |
| *B65D 85/00* | (2006.01) |
| *A61L 2/00* | (2006.01) |

(52) U.S. Cl.
CPC ............... *A61L 29/145* (2013.01); *A61L 2/08* (2013.01); *A61L 2/10* (2013.01); *A61L 29/085* (2013.01); *A61L 29/14* (2013.01); *A61M 25/002* (2013.01); *A61L 2/00* (2013.01); *A61L 2202/24* (2013.01); *B65D 85/70* (2013.01); *Y10T 428/1352* (2015.01)

(58) Field of Classification Search
CPC ....... A61L 29/14; A61L 2/00; A61M 25/002; Y10T 428/1334; Y10T 428/1341; Y10T 428/1352; Y10T 428/1376; Y10T 428/1379; Y10T 428/1383; B65D 85/70; A61J 1/00
USPC .......... 428/34.1, 35.2, 35.4, 35.7, 36.4, 36.5, 428/36.7, 36.8, 36.9, 36.91; 206/210, 570, 206/571

See application file for complete search history.

(56) References Cited

U.S. PATENT DOCUMENTS

| | | |
|---|---|---|
| 350,749 A | 10/1886 | Kernodle |
| 537,245 A | 4/1895 | Stock et al. |
| 551,514 A | 12/1895 | Sherman et al. |
| 3,648,704 A | 3/1972 | Jackson |
| 3,967,728 A | 7/1976 | Gordon et al. |
| 4,100,309 A | 7/1978 | Micklus et al. |
| 4,119,094 A | 10/1978 | Micklus et al. |
| 4,373,009 A | 2/1983 | Winn |
| 4,459,317 A | 7/1984 | Lambert |
| 4,626,292 A | 12/1986 | Sherman |
| 4,691,820 A | 9/1987 | Martinez |
| 4,729,914 A | 3/1988 | Kliment et al. |
| 4,792,914 A | 12/1988 | Dartois et al. |
| 4,906,237 A | 3/1990 | Johansson et al. |
| 5,001,009 A | 3/1991 | Whitbourne |
| 5,041,100 A | 8/1991 | Rowland et al. |
| 5,120,816 A | 6/1992 | Gould et al. |
| 5,160,790 A | 11/1992 | Elton |
| 5,240,675 A | 8/1993 | Wilk et al. |
| 5,242,428 A | 9/1993 | Palestrant |
| 5,322,667 A | 6/1994 | Sherman |
| 5,356,948 A | 10/1994 | Payne, Jr. et al. |
| 5,405,366 A | 4/1995 | Fox et al. |
| 5,529,727 A | 6/1996 | LaBombard et al. |
| 5,576,072 A | 11/1996 | Hostettler et al. |
| 5,604,189 A | 2/1997 | Zhang et al. |
| 5,618,492 A | 4/1997 | Auten et al. |
| 5,688,855 A | 11/1997 | Stoy et al. |
| 5,741,828 A | 4/1998 | Stoy et al. |
| 5,744,094 A | 4/1998 | Castberg et al. |
| 5,882,687 A | 3/1999 | Park et al. |
| 6,017,577 A * | 1/2000 | Hostettler et al. ........... 427/2.12 |
| 6,099,804 A | 8/2000 | Clausen et al. |
| 6,102,898 A | 8/2000 | Khan et al. |
| 6,409,717 B1 * | 6/2002 | Israelsson et al. ............ 604/544 |
| 6,629,961 B1 | 10/2003 | Israelsson et al. |
| 6,664,308 B2 | 12/2003 | Sun et al. |
| 6,986,868 B2 * | 1/2006 | Madsen ......................... 422/23 |
| 7,669,720 B2 | 3/2010 | Zhang et al. |

(Continued)

FOREIGN PATENT DOCUMENTS

| | | |
|---|---|---|
| EP | 0166998 A2 | 6/1985 |
| EP | 0093093 B1 | 3/1986 |
| 7,705,067 | B2 | 4/2010 Norton et al. |
| 2011/0034787 | A1 | 2/2011 Hagino et al. |

*Primary Examiner* — Walter B Aughenbaugh

(74) *Attorney, Agent, or Firm* — Coloplast Corp., Coloplast A/S; Nick Baumann

(57) ABSTRACT

A sterilized ready-to-use catheter includes a package, a catheter having a hydrophilic coating, and an aqueous solution in contact with the catheter inside of the package.

2 Claims, No Drawings

(56) References Cited

FOREIGN PATENT DOCUMENTS

| | | | |
|---|---|---|---|
| EP | 0217771 | A1 | 4/1987 |
| EP | 0379156 | A2 | 7/1990 |
| EP | 0389632 | A1 | 10/1990 |
| EP | 0454293 | A2 | 10/1991 |
| EP | 0698397 | A1 | 2/1996 |
| GB | 1600963 | A | 5/1978 |
| GB | 2284764 | A | 6/1995 |
| GB | 2319507 | A | 5/1998 |
| HU | P9602246 | A | 1/1997 |
| HU | 216246 | B | 5/1999 |
| HU | 9902969 | A2 | 1/2000 |
| JP | 54029343 | A | 3/1979 |
| JP | 60259269 | A | 12/1985 |
| JP | H489061 | A | 3/1992 |
| JP | 4255737 | A | 9/1992 |
| JP | H4285561 | A | 10/1992 |
| JP | H5192397 | A | 8/1993 |
| JP | 6007426 | A | 1/1994 |
| JP | H7250891 | A | 10/1995 |
| JP | 8066461 | A | 3/1996 |
| WO | WO8606284 | A1 | 11/1986 |
| WO | WO8909246 | A1 | 10/1989 |
| WO | WO9005162 | A1 | 5/1990 |
| WO | WO9119756 | A1 | 12/1991 |
| WO | WO9416747 | A1 | 8/1994 |
| WO | WO9426336 | A1 | 11/1994 |
| WO | WO9506670 | A1 | 3/1995 |
| WO | WO9521636 | A1 | 8/1995 |
| WO | WO9603164 | A1 | 2/1996 |
| WO | WO9623602 | A1 | 8/1996 |
| WO | WO9630277 | A1 | 10/1996 |
| WO | WO9726937 | A1 | 7/1997 |
| WO | WO9729160 | A1 | 8/1997 |
| WO | WO9811932 | A1 | 3/1998 |
| WO | WO9819729 | A1 | 5/1998 |
| WO | WO9858988 | A1 | 12/1998 |
| WO | WO9858989 | A1 | 12/1998 |
| WO | WO9858990 | A1 | 12/1998 |
| WO | WO0030696 | A1 | 6/2000 |

* cited by examiner

STERILIZED READY-TO-USE CATHETER

FIELD OF THE INVENTION

The present invention relates generally to sterilization of medical devices having hydrophilic coatings and more specific to sterilization using radiation. Furthermore, the invention relates to a sterilized set comprising a medical device provided with a hydrophilic coating and a liquid for wetting the hydrophilic coating, a method for protecting the hydrophilic coating of a medical device having such coating during sterilization using radiation as well as a medical device having a hydrophilic coating said medical device showing, after sterilization using radiation, a prolonged water drain off time and reduced friction force.

DESCRIPTION OF THE RELATED ART

It is known to coat medical devices, e.g., catheters for introduction into human cavities such as blood vessels, digestive organs and the urinary system, with a hydrophilic coating, normally as a minimum applied on that part of the surface which is introduced or comes into contact with mucous membranes, etc., during introduction of the device. Whereas such coating is not particularly smooth when dry, so that the handling of the device may become inconvenient, it becomes extremely slippery when it is swelled with water, preferably immediately before introduction into the human body and thus ensures a substantially painless introduction with a minimum of damage on tissue.

U.S. Pat. No. 3,967,728 to Gordon discloses the use of a sterile lubricant for deposition on and lubricating an uncoated catheter before use.

WO 86/06284 (Astra Meditech Aktiebolag) discloses a wetting and storing device for a coated catheter in which the coating may be wetted using water or water comprising common salt and possibly bactericidal compounds or other additives.

GB Patent Application No. 2 284 764 (MMG (Europe Ltd.)) discloses the application of a lubricious substance such as a water based jelly to the tip of a non-coated catheter prior to insertion into the urethra.

U.S. Pat. No. 3,648,704 (Jackson) discloses a disposable catheter apparatus in which a lubricant may be applied to the tip of the catheter prior to catherisation.

A large number of methods are known for the production of hydrophilic surface coatings for improving the slipperiness of a catheter or other medical device.

These methods are most often based on the fact that the substrate to be provided with a hydrophilic surface coating, in the course of one or more process stages with intermediary drying and curing, is coated with one or more (mostly two) layers, which are brought to react with one another in various ways, e.g. by polymerization initiated by irradiation, by UV light, by graft polymerization, by the formation of interpolymeric network structures, or by direct chemical reaction. Known hydrophilic coatings and processes for the application thereof are e.g. disclosed in Danish Patent No. 159,018, published European Patent Application Nos. EP 0 389 632, EP 0 379 156, and EP 0 454 293, European Patent No. EP 0 093 093 B2, British Patent No. 1,600,963, U.S. Pat. Nos. 4,119,094, 4,373,009, 4,792,914, 5,041,100 and 5,120,816, and into PCT Publication Nos. WO 90/05162 and WO 91/19756.

According to a method disclosed in U.S. Pat. No. 5,001,009, a hydrophilic surface coating is prepared on a substrate by applying, in two stages or in one combined stage, on the substrate a primer reactive with or adhesive to the substrate and then the actual hydrophilic surface layer which, in this case, comprises polyvinylpyrrolidone [PVP] as the active constituent. By this method, no chemical reaction takes place between the components of the two layers applied. When the product remains inside the body only for a short period, there may be a risk that water will be extracted from the hydrophilic surface coating and into the tissues of the surrounding mucous membranes etc., owing to a higher osmotic potential of said tissues. At the same time, there is a risk of abrasion of the coating during insertion. As a result of the extraction of water or loss of coating, the hydrophilic surface coating will have a tendency to become less slippery and to stick to surrounding tissues, and the removal of the medical device from the body may cause pain or damage the tissue. This is especially a problem when carrying out urodynamic examinations via a catheter.

European Patent No. EP 0 217 771 describes a method of forming a hydrophilic coating in order to retain the slipperiness in use for a longer period of time by applying a non-reactive hydrophilic polymer surface layer to a substrate, applying to the non-reactive hydrophilic surface polymer a solution comprising a solvent and above 2% (weight per volume) of an osmolality-increasing compound selected from the group consisting of mono and disaccharides, sugar alcohols, and non-toxic organic and inorganic salts, with the proviso that the osmolality-increasing compound is not a trihalogenide such as $KI_3$ ($KI/I_2$), and evaporating the solvent. EP 0 217 771 discloses that when wetting the catheters after drying, catheters having a coating of a non-toxic, osmolality increasing compound retaining their slipperiness for longer times than corresponding untreated surfaces i.e. coated catheters dry more slowly. However EP 0 217 771 is silent with respect to storing the coated catheters in the wetting solution and any type of sterilization or problems in connection herewith.

International patent publication No. WO 94/16747 discloses a hydrophilic coating with improved retention of water on a surface, especially a surface of a medical device such as a urethra catheter, prepared by applying to the surface in one or more process steps at least one solution of components that will combine to form the hydrophilic coating. During the final step, the surface is coated with an osmolality promoting agent which is dissolved or emulgated in the solution or in the last solution to be applied when forming the hydrophilic coating. WO 94/16747 does not disclose cross-linked coatings.

WO 89/09246 discloses solid shaped structures having a surface coated with crosslinked hydrophilic polymer, the coating being durable and exhibiting a low coefficient of friction when wet. It is stated that the degree of crosslinking is critical and is to be controlled by the operating conditions chosen as too much crosslinking reduces or completely eliminates the low friction surface property, and too little crosslinking negatively affects the durability of the coating. WO 89/09246 does not disclose the presence of a water soluble or osmolality-increasing compound in the coating.

WO 98/19729 discloses catheter packages wherein the catheter is stored in the wetting medium comprising, e.g., an aqueous solution of NaCl, but WO 98/19729 does not mention a wetting solution comprising a hydrophilic polymer.

All said coatings are developed for instant swelling immediately before use of the medical device on which the coatings are applied.

It has been found, however, that most hydrophilic coatings lose their water retention and that the coefficient of friction increase when the coatings are stored in water for an extended period of time and/or particulary after sterilisation using irradiation or autoclaving.

Thus, there is still a need for a hydrophilic coating retaining water retention and low coefficient of friction when the coatings are stored in water for an extended period of time and/or particularly after sterilisation using irradiation or autoclaving.

SUMMARY OF THE INVENTION

The present invention relates to a method for sterilizing a medical device comprising a hydrophilic coating using radiation.

Furthermore, the invention relates to a sterilized set comprising a medical device provided with a hydrophilic coating and an aqueous liquid for wetting the hydrophilic coating.

Still further, the invention relates to a method of protecting the hydrophilic coating of a medical device having such coating during sterilizing using radiation.

The invention further relates to a medical device comprising a hydrophilic coating said medical device showing, after sterilization using radiation, a prolonged water drain off time and a reduced friction force.

The invention yet further relates to methods for preparing sterilized catheters having hydrophilic coatings.

DETAILED DESCRIPTION OF THE INVENTION

The present invention relates to a method for sterilizing a medical device comprising a hydrophilic coating using radiation said method comprising the steps of bringing the medical device having such coating in contact with an aqueous liquid for wetting the hydrophilic coating, said liquid comprising a solution of a hydrophilic polymer and sterilizing the device by applying a sufficient amount of radiation.

It has surprisingly been found that the water retention can be increased dramatically and the coefficient of friction can be kept low by adding hydrophilic polymers for example polyvinylpyrrolidone or copolymers containing N-vinylpyrrolidone, poly(meth)acrylic acid or copolymers containing (meth)acrylic acid or (meth)acrylic acid esters, polyacrylamides, polyvinylalcohol and copolymers of partially saponified vinylacetate copolymers, polyethylenglycol, polyvinylmethylether, polyvinylmethylether-maleic anhydride and copolymers containing maleic-anhydride or maleic-acidesters or copolymers containing vinylmethyl-ether, or copolymers thereof, or water soluble polysaccharides or derivatives thereof such as carboxymethylcellulose (CMC) or hydroxyethylcellulose or Xanthane or a derivative thereof to the liquid for wetting a hydrophilic coating and that these compounds also protect these properties during exposure to sterilization using radiation when wetted with such wetting liquid.

Suitable hydrophilic polymers for the wetting agent may be mixtures of the preferred species stated above.

Without limiting the invention to any specific hypothesis, it is assumed that the effect may be ascribed to one or more of following effects:

1. Dissolved hydrophilic polymer chains in the aqueous liquid penetrate physically bound or crosslinked coatings and stabilise them. The thickness of the coating is increased which contributes to a higher capacity of retaining water.

2. Dissolved hydrophilic polymer chains in the aqueous liquid penetrates physically bound or crosslinked coatings and prevent further crosslinking during irradiation.

3. Dissolved polymers may be chemically bonded to the hydrophilic coating during irradiation in the aqueous liquid. This gives rise to a thicker layer of coating contributing to a higher capacity of retaining water.

It is preferred that the hydrophilic polymer is a synthetic polymer and especially that the hydrophilic polymer is at least compatible with and preferably of the same type as the hydrophilic polymer of the coating.

Also preferred are polysaccharides selected from the group consisting of cellulose derivatives and xanthans. Although polysaccharides show a tendency of break down on sterilisation using radiation, these compounds have still proven effective in giving a long retention time, a low friction. Normally such compounds show a very pronounced thickening effect in water and are used in relatively low amounts.

In a preferred embodiment of the invention the cellulose derivative is CMC or a derivative thereof. CMC is suitably used in an amount from 0.005 to 3.0%, depending on the molecular weight and degree of substitution of the polymer preferably about 0.5% giving very good results. When using xanthan, the amount used is normally in the range from 0.005 to 1%, preferably about 0.15%.

In an especially preferred embodiment of the invention the hydrophilic polymer is a polyvinyl pyrrolidone (PVP).

The amount of polyvinyl pyrrolidone to be used according to the invention may vary and depends i.a. on the molecular weight of the specific PVP. The higher the molecular weight, the higher is the tendency of gelling. Thus, the use of higher amounts of low molecular weight PVP gives an effect similar to the use of lower amounts of a higher molecular weight PVP. The amount of a PVP of a given molecular weight PVP to be used is easily determined by the skilled in the art by routine experiments testing the water retention. When using a PVP having a relatively low molecular weight above 1000 and preferably above 5000, an amount of 6% by weight has proven to be suitable giving a long retention time, a low friction and no problems with gelling.

It is also considered an aspect of the invention, when working with medical devices having physically bound or cross-linked hydrophilic coatings, to include a hydrophilic polymer not forming cross-links with the coating into the coating and to wet or store the medical device in water or saline.

Saline or another non-toxic osmolality increasing agent is preferably present in the physiological range. Thus, saline is preferably present in an amount of 0.9%

Furthermore, the invention relates to a sterilized set comprising a medical device provided with a hydrophilic coating and an aqueous liquid for wetting the hydrophilic coating wherein said device is in contact with the aqueous liquid, wherein said set has been sterilized using radiation while in contact with said liquid comprising a solution of a hydrophilic polymer.

In another embodiment of the set of the invention the aqueous liquid is placed in the package also comprising the medical device provided with a hydrophilic coating. Thus, the catheter is permanently wetted by the wetting liquid and thus ready to use. Such a set may be of the kind disclosed in WO 98/19729.

It has surprisingly been found that using wetting liquids of the kind disclosed above, it is possible to provide a catheter which is permanently wetted by the wetting liquid and thus ready to use and which may be sterilised by irradiation or autoclaving and which will retain the water retention capability and thus low coefficient of friction when the coatings are stored in water for an extended period of time.

Sterilization using radiation is normally carried out using beta or gamma radiation.

Normally, a loss of water retention capability of coated catheters is observed, probably due to loss of non-crosslinked and non-bonded polymer chains from the coating during storage in water or by further crosslinking of the coating during irradiation in water.

In the first case a collapse of the coating, when the device is removed from the water reservoir, will give a low water retention and increase of the coefficient of friction during use. In the second case further crosslinking will decrease the water content in the coating and hence, the coating will show a low water retention and an increased friction coefficient.

Still further, the invention relates in a third aspect to a method of protecting the hydrophilic coating of a medical device having such coating during sterilizing using radiation, characterized in that the coating is brought into contact with an aqueous solution comprising a hydrophilic polymer and exposed for the radiation while in contact with the aqueous solution.

In a fourth aspect, the invention relates to a medical device comprising a hydrophilic coating said medical device showing, after sterilization using radiation, a water drain off time >3 minutes and a friction force of <0.05 N when testing a 10 cm tube having the hydrophilic coating fixed on a stainless steel plate with two stainless steel rods as shown in ASTM 1894-93 for both physically bonded hydrophilic coatings of the type disclosed in WO 94/16747 and for chemically cross-linked coatings of the types disclosed in i.a. WO 98/58988, WO 98/58989, and WO 98/58990.

Using the invention it has proven possible to obtain and retain very high water drain off time and low friction forces.

In a fifth aspect, the invention relates to a method of preparing a sterilized catheter having a crosslinked two-layer hydrophilic coating comprising the steps of a) preparing a solution of polyvinyl pyrrolidone dissolved in an ethanol/gamma butyrolactone solvent mixture, b) dipping a raw catheter in the solution and letting it dry at ambient temperature, c) dipping the resulting catheter in a PVP-solution containing urea and an ethanol/gamma butyrolactone (85/15) solvent mixture, d) further drying at elevated temperature, e) cross-linking the polyvinylpyrrolidone by exposing the coated catheter to UV-light having a wave length range between 200 and 300 nm. for from ½ to 15 minutes, and f) sterilizing the coated catheter while wetted with a. solution of PVP by irradiation.

In a sixth aspect, the invention relates to a method of preparing a sterilized catheter having a crosslinked hydrophilic coating with unsaturated poly(methyl vinyl ether/maleic anhydride)/hydroxyethylmethacrylate (HEMA) prepolymers comprising the steps of a) preparing a solution of poly(methyl vinyl ether/maleic anhydride) in acetone in a reaction vessel equipped with at stirrer, keeping the reaction mixture at room temperature while adding 1-methylimidazole as a catalyst and hydroxyethylmethacrylate dropwise to the stirred polymer solution during a period of 30 minutes, b) stirring the mixture for from few minutes to 10 hours at room temperature, c) preparing a primer mixture by dissolving a medical grade polyurethane and the poly(methyl vinyl ether/maleic anhydride)/HEMA unsaturated prepolymer in a mixture of THF and acetone, d) coating a raw catheter with a primer by dipping in the resulting solution in a manner known per se, e) dipping the resulting catheter in the solution of poly (methyl vinyl ether/maleic anhydride)/HEMA unsaturated prepolymer in acetone for applying a top coat, f) drying the resulting catheter, g) cross-linking the poly(methyl vinyl ether/maleic anhydride)/HEMA unsaturated prepolymer polyvinylpyrrolidone by exposing the coated catheter to 5 M rads from a high energy electron beam source, and h) sterilizing the coated catheter while wetted with a. solution of PVP by irradiation.

In a seventh aspect, the invention relates to a method of preparing a sterilized catheter having a cross-linked single layer of hydrophilic coating comprising the steps of a) preparing a solution of polyvinyl pyrrolidone dissolved in an ethanol/gamma butyrolactone solvent mixture, b) dipping a raw catheter in the solution and letting it dry at elevated temperature, c) cross-linking the polyvinylpyrrolidone by exposing the coated catheter to UV-light having a wave length range between 200 and 300 nm. for from ½ to 15 minutes, and d) sterilizing the coated catheter while wetted with a. solution of PVP by irradiation.

In accordance with a preferred embodiment of the invention, the wetting liquid comprises an antibacterial agent such as a silver salt, e.g., silver sulphadiazine, an acceptable iodine source such as povidone iodine (also called polyvinylpyrrolidone iodine), chlorhexidine salts such as the gluconate, acetate, hydrochloride or the like salts or quaternary antibacterial agents such as benzalkonium chloride or other antiseptics or antibiotics. Antibacterial agents reduces the risk of infection, especially when performing urodynamic examinations.

The wetting liquid may according to the invention comprise an osmolality increasing agent such as urea, sodium chloride and/or any salt or organic low molecular weight compound being physiological acceptable and non-irritating for adjusting the ion strength of the coating approximately to the physiological range, the coating preferably being isotonic in use.

When using urea, the added amount may vary within very broad limits.

The wetting liquid of the invention may also, if desired, comprise plasticizers for the hydrophilic coating such as diethylene glycol, glycerol, phthalates, sorbitol or the like.

Indicators or buffers for pH or antibodies, e.g. monoclonal antibodies for specific proteins, may also be enclosed in the wetting liquid of the invention.

In accordance with a preferred embodiment pharmaceutically active compounds such as antioxidants or preservatives such as anti microbial agents or antithrombogenic agents may be added to the composition.

MATERIALS AND METHODS

Polyvinylpyrrolidone: PVP K 90 available from ISP Inc. having a molecular weight 1,300,000 according to ISP.

Polyvinylpyrrolidone: Plasdone K-25 available from ISP Inc. having a molecular weight 34,000 according to ISP.

Poly(methyl vinyl ether/maleic anhydride) is available as the Gantrez AN series of copolymers from ISP Ethanol: Absolute Alcohol.

Gamma butyrolactone: Gamma-butyrolactone from International Specialty Products.

UV catalyst: ESACURE KIP 150 from Lamberti SpA

Darocure® 1173 from Ciba Geigy.

Method for Determination of the Friction

The Standard Test Method for Static and Kinetic Coefficient of Friction of Plastic Film and Sheeting, ASTM D 1894-93 was modified for testing the friction coefficient and wear on plastic tubes and catheters.

The tubes or catheters were cut in lengths of 10 cm and fixed on a stainless steel plate with two stainless steel rods as shown in ASTM D 1894-93. The rods had diameters comparable with the inner diameter of the tubes or catheters to keep their shape even when heavy sledges were placed upon them.

The friction was determined after wetting after dipping the specimen in wetting liquid for 1 minute. The force for pulling the sledge was measured in Newtons.

Method for Determination of Water Retention

Water retention was determined by subjectively determining the time for the liquid to drain off after which the coating is dry using a stop watch.

EXPERIMENTAL PART

Example 1

Preparation of a Catheter Having a Crosslinked Two-Layer Hydrophilic Coating 5 parts of PVP K 90 and 0.05 part of ESACURE KIP 150 were dissolved in 94.95 parts of an ethanol/gamma butyrolactone solvent mixture. PVC-catheters were dipped in the solution and dried 1 minute at ambient temperature and then dipped in a PVP-solution containing 5 parts of PVP, 1 part of urea and 94 parts of an ethanol/gamma butyrolactone (85/15) solvent mixture. The catheters were further dried for 30 minutes at 70° C. and exposed to UV-light having a wave length range between 200 and 300 nm. for 5 minutes.

Finally, sterilization of the coated catheter was performed while wetted with a solution of PVP using irradiation.

Example 2

Preparation of a Catheter Having a Crosslinked Hydrophilic Coating with Unsaturated Poly(Methyl Vinyl Ether/Maleic Anhydride)/Hydroxyethylmethacrylate (HEMA) Prepolymers 20 parts of Gantrez® AN 119 was dissolved in 200 parts of acetone in a reaction vessel equipped with at stirrer. The reaction mixture was kept at room temperature. One drop of 1-methylimidazole was added to the solution as a catalyst. 5 mole % 2-hydroxyethylmethacrylate, based on contents of maleic anhydride were added dropwise to the stirred polymer solution during a period at 30 min. The mixture was stirred for further 2 hours at room temperature.

A 50:50 primer mixture with 5% solids was prepared by dissolving a medical grade polyurethane and the Poly(methyl vinyl ether/maleic anhydride)/HEMA unsaturated prepolymer in a 50:50 mixture of THF and acetone and was coated on PVC catheters as a primer by dipping in a manner known per se.

The catheters were dipped in the solution of poly(methyl vinyl ether/maleic anhydride)/HEMA unsaturated prepolymer in acetone for applying a top coat, dried and exposed to 5 M rads from a high energy electron beam source.

Afterwards, the cross-linked coatings were hydrolyzed and neutralized in a sodium hydrogen carbonate buffer solution for one hour before drying.

Then, sterilization of the coated catheter was carried out while wetted with a solution of PVP using irradiation.

The friction tested according to the modified ASTM D 1894-93 method as described above showed a friction force of 0.02 when determined in water.

Example 3

A top coat and a primer solution were prepared as in Example b. To the solutions was added 1% by weight of the solid Darocure® 1173, a UV photo-initiator obtainable from Ciba Geigy.

PVC catheters were dipped in the primer solution, dried for 30 minutes and dipped in the top coat solution also containing 1% by weight of the solid of Darocure® 1173 and dried for further 30 minutes. Then, the coating was cross-linked by exposure to UV light.

The cross-linked coatings were then hydrolyzed and neutralized in a sodium hydrogen carbonate buffer solution for one hour before drying.

Then, sterilization of the coated catheter was carried out while wetted with a. solution of PVP using irradiation.

The friction tested according to the modified ASTM D 1894-93 method as described above showed a friction force of 0.02 when determined in water.

Example 4

Preparation of a Catheter Having a Cross-Linked Single Layer Hydrophilic Coating According to the Invention 5 parts of PVP K 90 was dissolved in 95 parts of a ethanol/gamma butyrolactone (85/15) solvent mixture. PVC catheters were dipped in the solution, dried for 30 minutes at 70° C. and exposed to a UV light having a wave length between 200 and 300 nm for 6 minutes.

Then, sterilization of the coated catheter was carried out while wetted with a. solution of PVP using irradiation.

The catheter was lubricious in wet condition and had a high abrasion resistance.

Example 5

Determination of the Water Retention Time in Minutes and the Friction Force in N when Using the Aqueous Wetting Liquid According to the Invention as Compared to the Use of Saline for Wetting the Coating A cross-linked coating prepared according to Example a, and the following commercial catheters: an EasiCath® catheter, from Coloplast A/S, a LoFric® catheter from Astra AB, a PuriCath® catheter from Maersk Medical, an AquaCath® catheter from EMS, and a Uro-flo Silky catheter from Simcare were tested for determination of the water retention time and the friction. The coated catheters were compared to an uncoated raw catheter having no hydrophilic coating.

All catheters were stored in a 6% solution of PVP Plasdone K-25 or in saline and sterilized by irradiation, and water reretention of the coatings and the force of friction were determined as described above.

The results are summarized in the below Table 1:

TABLE 1

| | Liquid | | | | | |
| --- | --- | --- | --- | --- | --- | --- |
| | 0.9% saline | 6% Plasdone K-25 | 0.5% CMC | 0.15% Xanthane | 0.9% Saline | 6% Plasdone K-25 |
| Coating | Water retention (minutes) | | | | Friction Force (N) | |
| Example a | 1-3 | 9 | 9 | 9 | 0.06 | 0.04 |
| EasiCath ® | 1-2 | 7 | | | 0.1 | 0.04 |

TABLE 1-continued

| | Liquid | | | | | |
|---|---|---|---|---|---|---|
| | 0.9% saline | 6% Plasdone K-25 | 0.5% CMC | 0.15% Xanthane | 0.9% Saline | 6% Plasdone K-25 |
| Coating | Water retention (minutes) | | | | Friction Force (N) | |
| LoFric ® | 1-2 | 5-7 | | | 0.05 | 0.02 |
| PuriCath ® | 1-2 | 5 | | | 0.32 | 0.25 |
| AquaCath ® | 1-2 | 3 | | | 0.08 | 0.06 |
| Uro-flo Silky | 1-2 | 1-2 | | | 0.7 | 0.35 |
| Raw catheter | 0 | 0 | | | 0.8 | 0.8 |

Example 6

Determination of the Water Retention Time in Minutes and the Friction Force in N for the Same Wetting Liquids Before and after Sterilization Using Radiation The friction force and the water retention were determined as stated above after the catheters had been stored in the stated solutions for two days.

The results are stated in the below Tables 2 and 3.

TABLE 2

| | Water retention (Minutes) | | | |
|---|---|---|---|---|
| | Storage for 48 hours without sterilization | | Storage for 48 hours with sterilization | |
| Wetting Liquid Coating | 0.9% NaCl | 0.9% NaCl + Plasdone K25 | 0.9% NaCl | 0.9% NaCl + Plasdone K25 |
| Example a | 3 | 5 | 1-3 | 9 |
| EasiCath ® | 9 | 5 | 1-2 | 7 |
| LoFric ® | 9 | 5 | 1-2 | 5-7 |
| PuriCath ® | 9 | 5 | 1-2 | 5 |
| Raw catheter | 0 | 0 | 0 | 0 |

TABLE 3

| | Friction Force (N) | | | |
|---|---|---|---|---|
| | Storage for 48 hours without sterilization | | Storage for 48 hours with sterilization | |
| Wetting Liquid Coating | 0.9% NaCl | 0.9% NaCl + Plasdone K25 | 0.9% NaCl | 0.9% NaCl + Plasdone K25 |
| Example a | 0.04 | 0.13 | 0.06 | 0.04 |
| EasiCath ® | 0.08 | 0.09 | 0.1 | 0.04 |
| LoFric ® | 0.07 | 0.08 | 0.05 | 0.02 |
| PuriCath ® | 0.26 | 0.31 | 0.32 | 0.25 |
| Raw catheter | 0.8 | 0.8 | 0.8 | 0.8 |

The results presented in Tables 2 and 3 show that sterilization by beta irradiation of the catheters in an isotonic saline solution reduces the water retention and increases the friction force of the coatings whereas sterilization by irradiation of coated catheters stored in a isotonic saline solution comprising also 6% Plasdone K-25 does not adversely effect water retention or friction force of the coatings. This is the case for the coating prepared according to Example a as well as for commercial state of the art catheters.

What is claimed is:

1. A set comprising:
    a catheter comprising a hydrophilic coating;
    an aqueous solution comprising a hydrophilic dissolved in the aqueous solution, wherein the hydrophilic polymer is selected from the group consisting of polyvinylpyrrolidone, copolymers containing N-vinylpyrrolidone, poly(meth)acrylic acid, copolymers containing (meth)acrylic acid, (meth)acrylic acid esters, polyacrylamides, polyvinylalcohol, copolymers of partially saponified vinylacetate, polyethylene glycol, polyvinylmethylether, polyvinylmethylether-maleic anhydride, copolymers containing maleic-anhydride or maleic-acid esters, and copolymers containing vinylmethyl ether; and
    a package that contains the catheter and the aqueous solution, wherein the catheter and the aqueous solution with the hydrophilic polymer are contained inside of the package.
2. The set according to claim 1, wherein the hydrophilic polymer is polyvinylpyrrolidone or a copolymer thereof.

* * * * *

UNITED STATES PATENT AND TRADEMARK OFFICE
CERTIFICATE OF CORRECTION

| | |
|---|---|
| PATENT NO. | : 9,138,510 B2 |
| APPLICATION NO. | : 14/275910 |
| DATED | : September 22, 2015 |
| INVENTOR(S) | : Niels Joergen Madsen |

It is certified that error appears in the above-identified patent and that said Letters Patent is hereby corrected as shown below:

In the claims,

Column 10, line 38 should read: "an aqueous solution comprising a hydrophilic --polymer-- dissolved in"

Signed and Sealed this
Twenty-second Day of March, 2016

Michelle K. Lee
*Director of the United States Patent and Trademark Office*